(12) United States Patent
Changaris

(10) Patent No.: US 9,549,550 B2
(45) Date of Patent: Jan. 24, 2017

(54) METHOD AND COMPOSITION FOR LONG ACTING BACTERIAL SUPPRESSION ON SKIN

(76) Inventor: David Changaris, Louisville, KY (US)

( * ) Notice: Subject to any disclaimer, the term of this patent is extended or adjusted under 35 U.S.C. 154(b) by 764 days.

(21) Appl. No.: 12/609,231

(22) Filed: Oct. 30, 2009

(65) Prior Publication Data

US 2011/0105612 A1    May 5, 2011

(51) Int. Cl.
| | |
|---|---|
| *A01N 37/06* | (2006.01) |
| *A01N 37/02* | (2006.01) |
| *A01P 1/00* | (2006.01) |
| *A61K 9/00* | (2006.01) |

(52) U.S. Cl.
CPC ............. *A01N 37/06* (2013.01); *A61K 9/0014* (2013.01)

(58) Field of Classification Search
USPC .................................................. 514/560, 558
See application file for complete search history.

(56) References Cited

U.S. PATENT DOCUMENTS

| | | | |
|---|---|---|---|
| 5,021,183 A | 6/1991 | Saud et al. | |
| 6,007,831 A | 12/1999 | Fujiwara et al. | |
| 6,296,861 B1 * | 10/2001 | Perricone | 424/401 |
| 6,472,356 B2 | 10/2002 | Narula et al. | |
| 6,794,344 B2 | 9/2004 | Taylor et al. | |
| 7,074,418 B2 | 7/2006 | Changaris | |
| 7,276,260 B2 | 10/2007 | Ernst et al. | |
| 7,578,970 B2 | 8/2009 | Bowker | |
| 2007/0212380 A1 * | 9/2007 | Changaris | A61K 9/0014 424/400 |

OTHER PUBLICATIONS

Lin (Clinic Rev Allerg Immunol, 2007, 33, pp. 167-177).*
Byeon (Growth Inhibition of Foodborne and Pathogenic Bacteris by Conjugated Linoleic Acid, J. Agri. Food Chem, 2009, 57, pp. 3164-3172).*
Cogen (Skin microbiota; a source of disease or defense? British Journal of Dermatology, Mar. 2008, pp. 1-27).*

* cited by examiner

*Primary Examiner* — Kathrien Cruz
(74) *Attorney, Agent, or Firm* — Steve Witters; Witters & Associates

(57) ABSTRACT

The present disclosure relates to methods and compositions for suppressing the growth of microorganisms on selected areas of the skin for an extended period of time, such as one hour, twenty four hours, seventy two hours, or longer. An area of the skin is selected for the suppression of the growth of microorganisms and a microorganism growth suppressing agent is topically applied to the selected area of the skin. The microorganism growth suppressing agent may be comprised in a pharmacologically acceptable vehicle such as an emulsion or soap. The microorganism growth suppressing agent comprises free conjugated fatty acid such as conjugated linoleic acid.

21 Claims, 3 Drawing Sheets

| Microorganism Applied | Initial Well Population | Approximate log reduction by Superfatted CLA Soap x 0.5-72 h |
|---|---|---|
| Pseudomonas aeruginosa ATTC 15442 | $1.5 \times 10^9$ | -9.2 |
| Staphylococcus aureus (MRSA) ATTC 33691 | $1.6 \times 10^8$ | -6.2 |
| Candida albicans (yeast) ATCC 10231 | $3.2 \times 10^6$ | -6.5 |
| Enterococcus faecium (VRE) ATCC 51559 | $3.4 \times 10^8$ | -8.5 |

FIGURE 3

METHOD AND COMPOSITION FOR LONG ACTING BACTERIAL SUPPRESSION ON SKIN

FIELD

Aspects of the present disclosure generally relate to methods and compositions for suppressing bacterium and/or fungi growth on selected areas of the skin. More specifically, compositions comprising conjugated fatty acids may be used to provide long-acting bacterial suppression on selected areas of the skin.

BACKGROUND

Background information is for informational purposes only and does not necessarily admit that subsequently mentioned information and publications are prior art.

People are cognizant with the notion of microbes (i.e., microorganisms such as bacteria and fungi) as being potentially hazardous and their transmission from person to person. People come into contact with these potentially hazardous microbes on a daily basis. Once in contact with human hands, these microbes may be passed from individual to individual and, thus, may contribute to infections of open wounds on the skin and the spread of infectious and contagious diseases. One of the most common ways of preventing infection or transmitting such microbes is by washing or applying antimicrobial emollients.

Topical wound treatment compositions are well known. They may include wound debriders, wound cleaners, wound healing agents, topical anti-microbials, anti-fungals, and skin conditioning agents. Regardless of the specific use, wound treatment compositions need to stay on the skin surface and remain active for a sufficient period of time to allow the composition to perform.

An example of use of an antimicrobial material that requires long acting bacterial suppression on the skin, in addition to topical wound treatment compositions, is when a doctor performs surgery. During surgeries requiring a prolonged surgical time, persisting bacteria in the surgical site may begin to double at the rate of once every 10 minutes. Over several hours there may develop gross contamination which can cause infection of the surgical incision. Under such circumstances, it is helpful for the doctor to apply a long acting bacterial suppression material or composition on his or her hands as well as the patient's skin within the operative region.

As reflected in the literature, much is known about antimicrobial agents. For example, there are the so-called "natural" antibacterial actives, which may be referred to as natural essential oils. Additional known antimicrobial agents are antibacterial metal salts and other antimicrobial agents. Much is also known about antifungal agents as well, particularly compounds belonging to the imidazole class of compounds.

However, many of the agents and compounds currently known may not provide long acting bacterial suppression, have properties limiting their application, or may not be easily applied. What are needed are methods and compositions for long acting bacterial and/or fungal suppression.

SUMMARY

According to one aspect of the present disclosure, a method for suppressing bacterial or fungal growth in or on selected areas of skin is provided. The method comprises selecting areas of the skin for the suppression of bacterial or fungal growth and applying a bacteriostatic material to the selected areas of the skin. The bacteriostatic material may comprise a bacteriostat selected from the group consisting of conjugated fatty acids, esters of conjugated fatty acids, acetates of fatty acids, and combinations thereof.

In another aspect of the present disclosure, a method for suppressing the growth of microorganisms on selected areas of the skin is provided. The method comprises selecting at least one area of the skin for the suppression of the growth of microorganisms and topically applying a pharmacologically acceptable vehicle comprising a microorganism growth suppressing agent to each at least one selected area of the skin. The microorganism growth suppressing agent may consist essentially of conjugated linoleic acid and is applied to the selected areas of the skin in an amount effective to suppress the growth of microorganisms for at least one hour.

In a further aspect, a bacteriostatic composition is provided. The bacteriostatic composition comprises a vehicle which is pharmacologically acceptable for placing on skin or open wounds and a bacteriostat. The bacteriostat consists essentially of conjugated linoleic acid. The bacteriostat is effective in reducing the growth of bacteria in or on skin for at least one hour.

These and other features, aspects and advantages of the present disclosure will become better understood with reference to the following drawings, description and claims.

BRIEF DESCRIPTION OF THE DRAWINGS

FIG. 3 shows 6-9 log reductions in growth of *Pseudomonas*, MRSA *Staphylococcus*, Vancomycin resistant *Enterococcus*, and *Candida albicans* in the presence of superfatted potassium based CLA soap over 72 hours, of Example 2.

DETAILED DESCRIPTION

Figure 1:
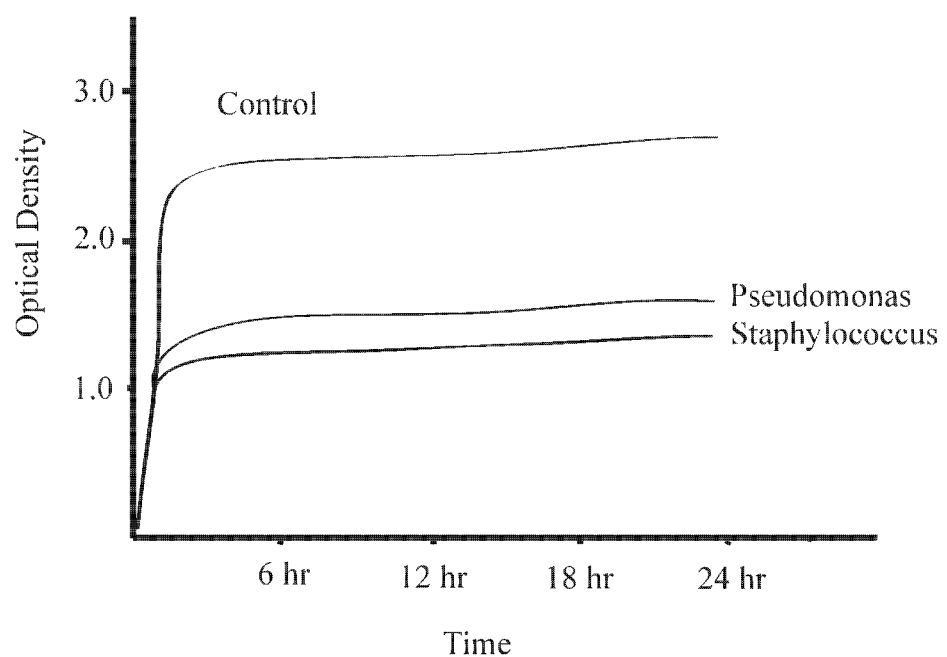
FIG. 1 shows the normal growth pattern of *Pseudomonas aeruginosa* (ATCC 15442) and *staphylococcus aureus* (ATCC 6366) against the persisting reduced rate of growth of added free fatty acid CLA, of Example 1.

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Various inventive features are described below that can each be used independently of one another or in combination with other features. However, any single inventive feature may not address any of the problems discussed above or may only address a subset of the problems discussed above. Further, one or more of the problems discussed above may not be fully addressed by any of the features described below.

Aspects of the present disclosure generally relate to methods for reducing bacterial and/or fungal growth on selected areas of the skin for an extended period of time. Aspects of the present disclosure also relate to compositions for reducing bacterial and/or fungal growth on selected areas of the skin for an extended period of time.

In at least one aspect, the present application discloses a method for reducing bacterial and/or fungal growth in or on a selected area of the skin by applying a bacteriostatic material comprising conjugated fatty acids, esters of conjugated fatty acids, acetates of fatty acids, and combinations thereof. For example, conjugated linoleic acid was unexpectedly found to have long acting bacteriostatic properties.

Conjugated fatty acids and methods of using as well as methods of preparing materials comprising conjugated fatty acids are disclosed in U.S. Pat. No. 7,074,418 and US patent publication #2007/0212380, both of which are incorporated by reference herein. U.S. Pat. No. 7,074,418 and US patent publication #2007/0212380 are incorporated by reference in their entirety herein, except for the prosecution thereof and words relating to the opinions and judgments of the author and words not directly relating to the technical details of the description of the aspects therein, are not incorporated by reference. The purpose of incorporating these publications is solely to provide additional information relating to technical features of one or more aspects, which information may not be completely disclosed in the wording in the pages of this application. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more aspects, are not to be incorporated by reference herein.

Conjugated fatty acids result from the shift of a double bond in the long chained fatty acid with two double bonds, predominantly in safflower oil and sunflower oil, the diene C18, linoleic acid. The linoleic acid molecule in its natural plant expressed state has two double bonds separated by a single carbon, which is saturated with hydrogen. Thus the molecules C9, C11 and C10, C12 linoleic acids represent two of the most common linoleic acids.

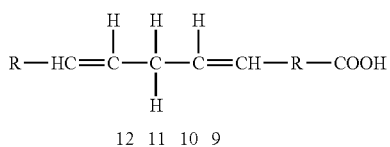

12 11 10 9

This unconjugated form permits the aliphatic and carboxyl ends to rotate around the C10 or C11. The conjugated form derived from alkalinization and extraction has the general formula:

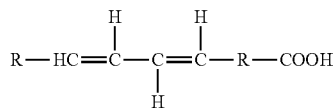

cis- or trans-9,11 conjugated linoleic acid

In this molecule the center is fixed in a cis or a trans position. The shape resembles a "boomerang" with a hydrophobic center that allows for the orientation of amphipathic molecules and the semi-rigidity of the emulsion. Both cis and trans molecules may contribute to the processes and compositions disclosed herein.

Currently, conjugated linoleic acid (CLA) remains an essential fatty acid often missing from our diet. Oral supplementation is well known to increase muscle mass and reduce body fat. CLA may have cardiovascular and cancer benefits. However, it was heretofore unknown and unexpected that CLA has properties for reducing bacterial and/or fungal growth on selected areas of the skin for an extended period of time.

It is shown herein that conjugated linoleic acid inhibits the growth of pathogenic bacteria and *Candida*. This C-18 dienic fatty acid is structurally similar to stearic acid (absent two double bonds in critical mid molecular position), another C-18 molecule. Stearic acid is a component of the membrane of cells. CLA may have the properties for reducing bacterial and/or fungal growth by interfering with the normal metabolism of C-18 molecules of pathogenic bacteria and fungi.

Aspects of the present disclosure relate to compositions of conjugated fatty acids which may inhibit the growth of pathogenic bacteria and/or fungi on normal and infected skin. This C-18 dienic fatty acid, its glycerides and metal salts, may reduce the rate of growth of mammalian pathogenic bacteria and/or fungi for many hours. The present disclosure teaches that direct application of oils comprising conjugated fatty acid (CFA), superfatting of soaps with CFA and the application thereof, and the application of emulsions made with CFA, such as congeners of conjugated linoleic acid. The application of aspects of the present disclosure may reduce the growth of pathogenic bacteria and fungi for hours, on and/or within skin. For example, CFA or CLA may be applied directly to the skin, or in a pharmacological acceptable vehicle such as a superfatted soap or emulsion, to reduce the growth rate of bacteria for one or more hours, in one hour increments, up to and including 1 hour, 24 hours, 72 hours, or even longer, such as several days.

In at least one aspect, a method for long acting bacterial suppression on normal and infected skin is provided. In at least one other aspect, compositions comprising conjugated linoleic acid having the capacity to reduce growth rate of pathogenic bacteria and/or fungi in normal and infected skin for one or more hours, in one hour increments, up to 72 hours, or longer, are provided.

In another aspect of the present disclosure, emollients for skin and methods of use, such as emollients comprising conjugated fatty acids and its congeners that may absorb through or onto skin, are provided. In at least one more aspect of the present disclosure, methods of using conjugated linoleic acid and its congeners to reduce the growth rate of pathogenic bacteria and fungi are provided. Other aspects of the present disclosure include emollients, soaps, emulsions, or other pharmacological acceptable vehicles comprising CFA or CLA, and its congeners for the reduction of the growth rate of pathogenic bacteria and/or fungi.

An emulsion may be prepared by a method as disclosed in U.S. Pat. No. 7,074,418. For example, a minimum number of chemicals and mechanical steps may used to create an emulsion. An emulsion may be created with conjugated fatty acid isomers admixed with amino acids and water alone. A mixture of metal hydroxide solutions of amino acids and peptides may form emulsions with conjugated fatty acid preparations that may lend itself to oral ingestion, transdermal, and parenteral injection. Certain amino acids, for example, aspartic acid and threonine, may be solubilized in high concentration in sodium and potassium hydroxide and stored for long periods at −20° to 0° Celsius. In at least one aspect, CLA is added to the emulsion in an amount greater than any metal halide or other material that may neutralize the biostatic effects of the CLA.

CFA, acylated CFA and similar molecules may form paste or mechanical mixture with various amino acids and amphipathic molecules that when mixed with water may form stable emulsions for ingestion, transdermal delivery, parenteral administration, storage and purification. High concentrations of amino acids in metal hydroxide solutions may be made into stable emulsions and/or pastes by the simple admixture of conjugated linoleic acid. This may result from the conjugated internal R—C=C—C=C—RCOOH and may be preserved in other unsaturated long chained fatty acids with similar internal conjugations which may be present to varying degrees in plant oils, and are therefore encompassed by the present disclosure. The CFA may be of a higher concentration than any metal halide which may improve the bacterial suppression of the mixture.

In one aspect of an emulsion, the emulsion comprises CFAs, amino acids and water. The water is preferably found at a concentration of from about 0.01% to about 90% w/v. The CFAs are preferably found at a concentration of between about 0.1% and about 70% w/v and more preferably at a concentration of from about 0.1% and about 50% w/v. Preferred CFAs include conjugated linoleic acids, for example, 9,11-octadecadienoic acid methyl ester, and 10,12-octadecadienoic acid methyl ester. The amino acids are preferably found at a concentration within the emulsion of between about 1% and about 70% w/v and more preferably at a concentration of between about 15% and about 40% w/v, and even more preferably at a concentration of between about 25% and about 35% w/v. Examples of amino acids useful in the emulsion include, but are not limited to proline, tyrosine, lysine, phenylalanine, leucine, iso-leucine, tryptophan, 5-hydroxytryptophan, arginine, glutamine, glycine, methionine, threonine and combinations thereof. The concentration of certain amino acids within the emulsion can be increased by first solubilizing the amino acids in a metal salt solution, for example, a solution of sodium hydroxide or potassium hydroxide. In at least one aspect, the emulsion comprises free CFA, CFA not associated with a metal halide or other constituent which may inhibit the bacteriostatic effects of the CFA.

In another aspect, the emulsion comprises CFAs, one or more macromolecules, and water. The water is preferably found at a concentration of from about 30% to about 99.9% w/v. The CFAs and macromolecules are together preferably found at a concentration of between about 0.1% and 70% w/v and more preferably at a concentration of from about 0.1% and 50% w/v and even more preferably from about 0.1% and 40% w/v. Preferred CFAs include conjugated linoleic acids, for example, 9,11-octadecadienoic acid methyl ester and 10,12-octadecadienoic acid methyl ester. The macromolecules found in the emulsion can be, for example, amino acids, deoxyribonucleic acids, ribonucleic acids, carbohydrates and/or peptides. Examples of amino acids useful in the emulsion include, but are not limited to, proline, tyrosine, lysine, leucine, iso-leucine, phenylalanine, tryptophan, 5-hydroxytryptophan, arginine, glutamine, glycine, methionine, threonine and combinations thereof. The concentration of certain amino acids within the emulsion can be increased by first solubilizing the amino acids in a metal salt solution, for example, a solution of sodium hydroxide or potassium hydroxide. Examples of preferred carbohydrates useful as macromolecules in the emulsions of the present disclosure include, but are not limited to, ribose, sucrose and fructose. Examples of preferred peptides useful as macromolecules in the emulsions of the present disclosure include, but are not limited to glutathione, aspartame, met-enkephalin and leu-enkephalin. In another aspect of the present disclosure, an amount of CFA is free of any metal halide or other component that may tend to neutralize or reduce the bacterial suppression effects of the CFA.

Another vehicle that may used to apply long acting bacterial suppression constituents disclosed herein is soap. Soap may be liquid or solid, typically in the form of a bar, and may comprise conjugated fatty acids, its esters, or acetates, in an amount sufficient to provide long acting microbe growth suppression in or on selected areas of the skin to which it is applied.

Soap bars for washing are typically prepared by neutralizing fatty acids with an aqueous solution of a base such as sodium hydroxide, potassium hydroxide, or an alkanolamine. The fatty acids are typically derived from natural sources, such as beef tallow, mutton tallow, palm oil, olive oil, palm kernel oil, and coconut oil, among others. These natural sources contain fatty acid components which are predominantly of even chain length due to the biochemical synthesis mechanism of living organisms.

Commercial soap bars are typically produced from blends of naturally derived fatty acids chosen to optimize specific performance characteristics, such as lathering. Soap formed from lower molecular weight saturated fatty acids in the range of about 8 to 12 carbon atoms may produce a bar which rapidly generates large quantities of bubbles which quickly break on continued lathering. Higher molecular weight saturated fatty acids in the 14 to 18 carbon may produce soap bars which slowly generate a dense, creamy, stable foam on lathering. A bar produced from predominantly short chain fatty acid soaps may have a relatively short lifetime because the soap may dissolve more rapidly in water. Conversely, long chain saturated fatty acid soaps may be relatively less soluble and a bar produced therefrom may have a longer lifetime.

Commercial soap manufacturers may typically employ a fatty acid blend comprised of about 80% tallow fatty acid and about 20% coconut-type fatty acid. Bars of soap may be produced by heating and melting fatty acid blends. A molar equivalent amount of a metal halide (e.g. sodium or potassium) in water solution may then be brought to the temperature of the melted fatty acid blend and mixed therewith. The viscous molten soap may then be poured into a pan or mold and permitted to cool and air dry until a desired moisture level is obtained. The cooled and dried soap may then be further shaped as desired.

The addition of a molar equivalent of the metal halide with the fatty acids may act to neutralize the fatty acids. Superfatting soaps or superfatted soaps, as used herein, refers to the addition of excess fatty acid beyond the one metal halide to one fatty acid in the soap making process. Superfatting of soaps has the net effect of the leaving the soaps with free fatty acid. This free fatty acid may attach to skin to reduce the stripping effects of soap, e.g. lye soaps. Superfatted soaps may increase the lathering of common soap comprising commonly used medium sized chained fatty acids found in coconut oil. In one aspect, the present disclosure relates to the free fatty acid CLA that may be applied to the skin alone or in some pharmacologically acceptable vehicle. In another aspect, the superfatted alkali metal salt potassium CLA may effectively clean the skin and hair, while leaving a coating of CLA on the skin or hair. This fine residual coating may then inhibit the growth of pathogenic bacteria.

One feature or aspect of an embodiment is believed at the time of the filing of this patent application to possibly reside broadly in a method for reducing bacterial and fungal growth in or on skin for hours by applying conjugated fatty acids (5%-100%), its esters, or acetates directly to normal or infected skin, either alone or in a pharmacologically acceptable vehicle.

Another feature or aspect of an embodiment is believed at the time of the filing of this patent application to possibly reside broadly in a method for reducing bacterial and fungal growth on or within skin for hours by applying conjugated linoleic acids (about 0.001% to about 5%), its esters, or acetates directly to normal or infected skin, either alone or in a pharmacologically acceptable vehicle.

Yet another feature or aspect of an embodiment is believed at the time of the filing of this patent application to possibly reside broadly in a method for reducing bacterial and fungal growth on or within skin for hours by applying mono-, di-, or tri-glyceride conjugated linoleic oils (5-100%), either alone or in a pharmacologically acceptable vehicle.

Still another feature or aspect of an embodiment is believed at the time of the filing of this patent application to possibly reside broadly in a method for reducing bacterial and fungal growth on or within skin for hours by applying mono-, di-, or tri-glyceride conjugated linoleic oils (0.001% to approximately 5%), either alone or in a pharmacologically acceptable vehicle.

A further feature or aspect of an embodiment is believed at the time of the filing of this patent application to possibly reside broadly in a method for reducing bacterial and fungal growth on or within skin for hours by washing skin with soap made with superfatted conjugated linoleic acid (5-100%), either alone or in a pharmacologically acceptable vehicle.

Another feature or aspect of an embodiment is believed at the time of the filing of this patent application to possibly reside broadly in a method for reducing bacterial and fungal growth on or within skin for hours by washing skin with soap made with superfatted conjugated linoleic acid (0.001% to approximately 5%), either alone or in a pharmacologically acceptable vehicle.

Yet another feature or aspect of an embodiment is believed at the time of the filing of this patent application to possibly reside broadly in a method for reducing bacterial and fungal growth on or within skin for hours by applying emulsions made with conjugated linoleic acid, its esters, its acetates, its glycerides (1%-99%), either alone or in a pharmacologically acceptable vehicle.

Still another feature or aspect of an embodiment is believed at the time of the filing of this patent application to possibly reside broadly in a method for reducing bacterial and fungal growth on or within skin for hours by applying emulsions made with conjugated linoleic acid, its, esters, its acetates, its glycerides (0.001% to approximately 5%), either alone or in a pharmacologically acceptable vehicle.

EXAMPLES

The following examples are included to demonstrate aspects of the present disclosure. It should be appreciated by those of skill in the art that the techniques disclosed in the examples that follow represent techniques discovered by the inventor to function in the practice of the disclosure, and thus can be considered to constitute selected modes for its practice. However, those of skill in the art should, in light of the present disclosure, appreciate that many changes can be made in the specific aspects that are disclosed and still obtain a like or similar result without departing from the spirit and scope of the disclosure.

Example 1

Conjugated linoleic acid (80%) and conjugated linoleic acid diglyceride, containing both trans and cis isomers, were used to show persisting reduction of bacterial growth over several hours. Each measure was accomplished in separate wells. Each well received a unique combination of the following, including controls.

Conjugated linoleic acid 80% and conjugated linoleic acid diglyceride, 25 uL were each separately added to Trypticase Soy Broth (TSB). To each solution was added 75 uL TSB plus 50 uL *staphylococcus aureus* (ATCC 6366) or *pseudomonas aeruginosa* (ATCC 15442). This was then entered into a 27 hour kinetic assay using a redox active dye to monitor growth. Appropriate controls were simultaneously run.

Figure 2:
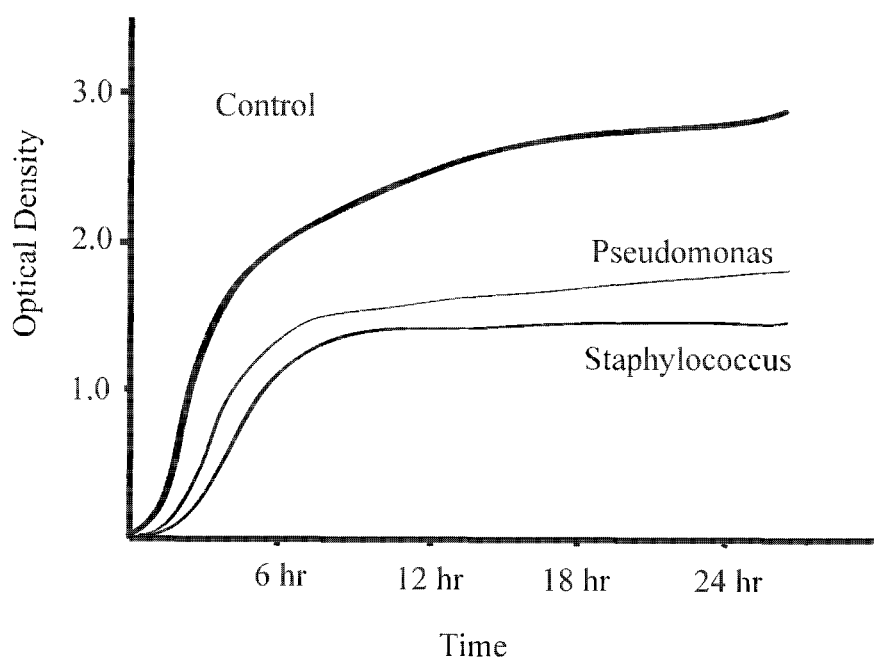
FIG. 2 shows the normal growth pattern of *Pseudomonas aeruginosa* (ATCC 15442) and *staphylococcus aureus* (ATCC 6366) against the persisting reduced rate of growth of added diglyceride conjugated linoleate, of Example 1.

The results for *staphylococcus aureus* unexpectedly show a reduction in bacterial growth beginning at 30 minutes, sustained for 20 hours. The results for *pseudomonas aeruginosa* unexpectedly show a reduction in bacterial growth beginning at 200 minutes, sustained for 27 hours. The results are graphically shown in FIGS. 1 and 2. FIG. 1 shows conjugated linoleic free fatty acid effect on *pseudomonas* and *staphylococcus* and FIG. 2 shows conjugated linoleic diglyceride effect on *pseudomonas* and *staphylococcus*.

Example 2

Superfatted conjugated linoleic acid soap (500 ml of water containing 20 g potassium hydroxide and 20 g aspartic acid added to 105 g CLA free fatty acid) was used to show the unexpected persisting reduction of bacterial growth over several hours.

An overnight culture of each organism to be tested was added to aliquots of the CLA soap along with TSB (a growth media for bacteria). These samples were placed in a bactometer cartridge and subsequently placed in the bactometer at 30° C. for 72 hours. The electrical impedance readings over time were measured to generate a growth curve. The microbes tested were *pseudomonas aeruginosa* ATCC 15442, *staphylococcus aureus* (methicillin resistant) ATCC 33591, *candida albicans* ATCC 10231, and *enterococcus faecium* (vancomycin resistant) ATCC 51559. The total volume of each well was 1.5 ml, 0.5 ml soap or TSB, and 0.5 ml TSB growth medium.

The results for *pseudomonas* shows a 9.1 log reduction in bacteria beginning at 1 hour and extending to 72 hours. The results for *Staphylococcus* shows a 6.1 log reduction in growth beginning at 1 hour and extending to 72 hours. The results for *candida* shows a 6.5 log reduction in growth beginning at 1 hour and extending to 72 hours. The results for *enterococcus* shows a 8.5 log reduction in growth beginning at 1 hour and extending to 72 hours. Culture control measures included measures with and without the CLA soap of the initial density of organisms with serial dilutions of bacteria. The results are shown in FIG. 3 wherein superfatted potassium CLA soap was shown to reduce the initial population of multiple microbes, 6-9 logs, for 72 hours, with initial effects shown at 60 minutes.

This significant reduction in bacterial growth shows that free CLA in superfatted soap significantly reduces the growth rate of bacteria over an extended period of time. Even though the bacteriostatic effects of CLA were measured for 72 hours, a longer period of effectiveness, such as 4 days or even longer, may be obtained.

Example 3

CLA free fatty acid oil was applied twice daily directly to skin with acne. After 24 hours, unexpectedly, there was substantial reduction in the size and redness of the acne.

It is known in the art that sebaceous glands may produce sebum which may build up behind the blockage of blocked skin pores. This built up sebum may harbor various forms of acne causing bacteria, including *Propionibacterium* acne and other bacteria. Therefore, this example shows that CLA is effective in reducing the growth rate of acne causing bacteria.

Example 4

An emulsion was prepared with diglyceride conjugated linoleic acid and amino acids after the method of Changaris (U.S. Pat. No. 7,074,418), and was applied to an open burn wound. The open wound was shown to heal without infection.

This example shows that diglyceride conjugated linoleic acid is effective in reducing the growth rate of microorganisms which may cause infections in open wounds and that its effectiveness remains for a period of time sufficient to ward off infection of the wound.

Example 5

A teenager with subacute acne for several weeks, over his back, was given the potassium soap described in Example 2 to wash daily. This application resolved his acne in two to three days. Additionally, alkali metal soap with superfatted CLA was used to wash the back of one teenager with multiple acne, over a period of 5-10 days, in which time the acne cleared.

These examples show that CLA in supperfatted soap, superfatted with CLA, is effective in reducing the growth of acne causing bacteria.

The present disclosure relates to compositions of conjugated fatty acids, and methods of use, which inhibit the growth of pathogenic microorganisms such as bacteria and fungi on normal and infected skin. This C-18 dienic fatty acid, its glycerides and metal salts, may reduce the rate of growth of mammalian pathogenic bacteria and fungi for many hours, or even days, in one hour increments. This disclosure teaches that direct application of oils, superfatting of soaps with such, as well as the application of emulsions made with congeners of conjugated linoleic acid reduce the growth of pathogenic bacteria and/or fungi for hours on or in skin.

It should be understood that the foregoing relates to exemplary aspects of the disclosure and that modifications may be made without departing from the spirit and scope of the disclosure as set forth in the following claims.

The invention claimed is:

1. A method for suppressing pathogenic bacterial growth in or on a selected area of skin or open wound, said method comprising the steps of:
   selecting an area of the skin or open wound having pathogenic bacterial growth for the suppression of the pathogenic bacterial growth;
   applying a pathogenic bacteriostatic material comprising a pathogenic bacteriostat selected from the group consisting of conjugated linoleic acid, esters of conjugated linoleic acid, salts of conjugated linoleic acid, acetates of conjugated linoleic acid, and combinations thereof, to said selected area of the skin or said open wound having the pathogenic bacterial growth therein or thereon; and
   suppressing the pathogenic bacterial growth in or on said selected area of the skin or said open wound for at least 30 minutes.

2. The method of claim 1 wherein said pathogenic bacteriostatic material suppresses the pathogenic bacterial growth in or on said selected area of the skin or said open wound for at least 72 hours.

3. The method of claim 1 wherein said pathogenic bacteriostatic material comprises a pathogenic bacteriostat selected from the group consisting of mono-glyceride conjugated linoleic oils, di-glyceride conjugated linoleic oils, tri-glyceride conjugated linoleic oils, and combinations thereof.

4. The method of claim 1 wherein said pathogenic bacteriostatic material comprises a pharmacologically acceptable vehicle.

5. The method of claim 4 wherein said pharmacologically acceptable vehicle is a soap.

6. The method of claim 5 wherein said soap is superfatted soap comprising said pathogenic bacteriostat in excess of any counter ions in said soap.

7. The method of claim 4 wherein said pharmacologically acceptable vehicle is an emulsion.

8. The method of claim 7 wherein said emulsion comprises said pathogenic bacteriostat in excess of any counter ions in said emulsion.

9. The method of claim 4 wherein said pathogenic bacteriostatic material comprises said pathogenic bacteriostat in an amount effective to reduce the growth rate of infection causing bacteria.

10. The method of claim 4 wherein said pathogenic bacteriostatic material comprises said pathogenic bacteriostat in an amount effective to reduce the growth rate of pimple causing bacteria.

11. A method for suppressing pathogenic bacterial growth in or on at least one selected area of the skin or open wound, said method comprising the steps of:
   selecting at least one area of the skin or open wound having pathogenic bacterial growth, for the suppression of the growth of the pathogenic bacteria;
   topically applying a pharmacologically acceptable vehicle comprising a pathogenic bacterial growth suppressing agent to each said at least one selected area of the skin or said open wound having the pathogenic bacterial growth therein or thereon;
   said pathogenic bacterial growth suppressing agent comprising conjugated linoleic acid; and
   said pathogenic bacterial growth suppressing agent being applied to each said at least one selected area of the skin or said open wound in an amount effective to suppress the growth of the pathogenic bacteria for at least 30 minutes.

12. The method for suppressing pathogenic bacterial growth of claim 11 wherein said pathogenic bacterial growth suppressing agent is applied to each said at least one selected area of the skin or said open wound in an amount effective to suppress the growth of the pathogenic bacteria for at least 72 hours.

13. The method for suppressing pathogenic bacterial growth of claim 12 wherein said pharmacologically acceptable vehicle is a soap, said soap being superfatted with said pathogenic bacterial growth suppressing agent, said conjugated linoleic acid being comprised within said soap in an amount in excess of counter ions comprised within said soap.

14. The method for suppressing pathogenic bacterial growth of claim 12 wherein said pharmacologically acceptable vehicle is an emulsion, said emulsion comprising an amount of free conjugated linoleic acid.

15. The method of claim 1 wherein said pathogenic bacteriostatic material consists essentially of said pathogenic bacteriostat, said pathogenic bacteriostat being selected from the group consisting of mono-glyceride conjugated linoleic oils, di-glyceride conjugated linoleic oils, tri-glyceride conjugated linoleic oils, and combinations thereof.

16. A method for suppressing pathogenic bacterial growth in or on a selected area of skin or open wound, said method comprising the steps of:
    selecting an area of the skin or open wound having pathogenic bacterial growth for the suppression of the pathogenic bacterial growth;
    applying a pathogenic bacteriostatic material consisting of conjugated linoleic acid to said selected area of the skin or said open wound having the pathogenic bacterial growth therein or thereon; and
    suppressing the pathogenic bacterial growth in or on said selected area of the skin or said open wound for at least 30 minutes.

17. The method for suppressing pathogenic bacterial growth of claim 1 wherein said pathogenic bacterial growth is Staphylococcus aureus growth.

18. The method for suppressing pathogenic bacterial growth of claim 1 wherein said pathogenic bacterial growth is Pseudomonas aeruginosa growth.

19. The method for suppressing pathogenic bacterial growth of claim 1 wherein said pathogenic bacterial growth is Enterococcus faecium growth.

20. The method for suppressing pathogenic bacterial growth of claim 1 wherein said pathogenic bacterial growth is acne causing bacterial growth.

21. The method for suppressing pathogenic bacterial growth of claim 20 wherein said pathogenic bacterial growth is Propionibacterium acne growth.

\* \* \* \* \*